United States Patent
Esquinas Fernandez et al.

(10) Patent No.: US 11,900,605 B2
(45) Date of Patent: Feb. 13, 2024

(54) METHODS AND SYSTEMS FOR DETECTING FOCAL LESIONS IN MULTI-PHASE OR MULTI-SEQUENCE MEDICAL IMAGING STUDIES

(71) Applicant: MERATIVE US L.P., Ann Arbor, MI (US)

(72) Inventors: Pedro Luis Esquinas Fernandez, Etobicoke (CA); Yi-Qing Wang, Paris (FR); Giovanni John Jacques Palma, Paris (FR)

(73) Assignee: MERATIVE US L.P., Ann Arbor, MI (US)

( * ) Notice: Subject to any disclaimer, the term of this patent is extended or adjusted under 35 U.S.C. 154(b) by 307 days.

(21) Appl. No.: 17/490,316

(22) Filed: Sep. 30, 2021

(65) Prior Publication Data

US 2023/0101975 A1 Mar. 30, 2023

(51) Int. Cl.
| | |
|---|---|
| *G06T 7/00* | (2017.01) |
| *A61B 6/03* | (2006.01) |
| *G06T 7/30* | (2017.01) |
| *G06T 7/13* | (2017.01) |

(52) U.S. Cl.
CPC ............ *G06T 7/0014* (2013.01); *A61B 6/032* (2013.01); *G06T 7/13* (2017.01); *G06T 7/30* (2017.01);
(Continued)

(58) Field of Classification Search
CPC .......... G06T 7/0014; G06T 7/30; G06T 7/13; G06T 2207/10081; G06T 2207/20221; G06T 2207/30096; A61B 6/032
See application file for complete search history.

(56) References Cited

U.S. PATENT DOCUMENTS

| | | | |
|---|---|---|---|
| 7,840,046 B2 | 11/2010 | Jerebko et al. | |
| 8,229,188 B2 * | 7/2012 | Rusko | A61B 5/4244 |
| | | | 382/128 |
| 8,885,898 B2 * | 11/2014 | Liu | G06F 18/22 |
| | | | 382/128 |

(Continued)

FOREIGN PATENT DOCUMENTS

| | | |
|---|---|---|
| WO | 2003/030074 | 4/2003 |
| WO | 2016/039891 A1 | 3/2016 |
| WO | WO-2023041167 A1 * | 3/2023 |

OTHER PUBLICATIONS

Ruskó, László, György Bekes, and Márta Fidrich. "Automatic segmentation of the liver from multi-and single-phase contrast-enhanced CT images." Medical Image Analysis 13.6 (2009): 871-882.*

(Continued)

*Primary Examiner* — Shefali D Goradia
(74) *Attorney, Agent, or Firm* — Michael Best & Friedrich LLP

(57) ABSTRACT

Methods and systems are provided for detecting focal lesions in multi-phase or multi-sequence medical imaging studies of medical images. One system includes memory for storing medical images and an electronic processor. The electronic processor is configured to: detect native candidate lesions for first phase computer tomography (CT) scans, detect candidate lesions for second phase CT scans, and project the candidate lesions detected for the first phase CT scans and/or the second phase CT scans on a same common domain. Once the candidate lesions are registered together, the electronic processor performs a matching algorithm for each of the native candidate lesions of the first phase CT scans with the registered candidate lesions from the second phase CT scans to determine presence and contours of valid lesions for the medical images, and to discard candidate lesions that are not acceptable.

20 Claims, 6 Drawing Sheets

(52) U.S. Cl.
CPC .............. *G06T 2207/10081* (2013.01); *G06T 2207/20221* (2013.01); *G06T 2207/30096* (2013.01)

(56) References Cited

U.S. PATENT DOCUMENTS

| | | |
|---|---|---|
| 2016/0098833 A1* | 4/2016 | Tsadok .................. G06T 3/0093 382/128 |
| 2017/0231550 A1 | 8/2017 | Do et al. |
| 2018/0306882 A1 | 10/2018 | Li et al. |
| 2020/0193244 A1 | 6/2020 | Zhou et al. |
| 2021/0098113 A1 | 4/2021 | Sorenson et al. |

OTHER PUBLICATIONS

Lai et al., "Hetero-Modal Learning and Expansive Consistency Constraints for Semi-Supervised Detection from Multi-Sequence Data," arXiv:2103.12972, Mar. 2021, 13 pages.

Lai et al., "Liver Tumor Localization and Characterization from Multi-Phase MR Volumes Using Key-Slice Parsing: A Physician-Inspired Approach," arXiv:2012.06964v3, Dec. 2020, 14 pages.

Hou et al., "Harvesting, Detecting, and Characterizing Liver Lesions from Large-scale Multi-phase CT Data via Deep Dynamic Texture Learning," arXiv:2006.15691v2, Jun. 2020, 10 pages.

International Search Report and Written Opinion for Application No. PCT/US2022/045315 dated Jan. 27, 2023 (8 pages).

Zhou et al., "Automatic detection and classification of focal liver lesions based on deep convolutional neural networks: a preliminary study," Frontier in Oncology, 2021, 10: 581210.

\* cited by examiner

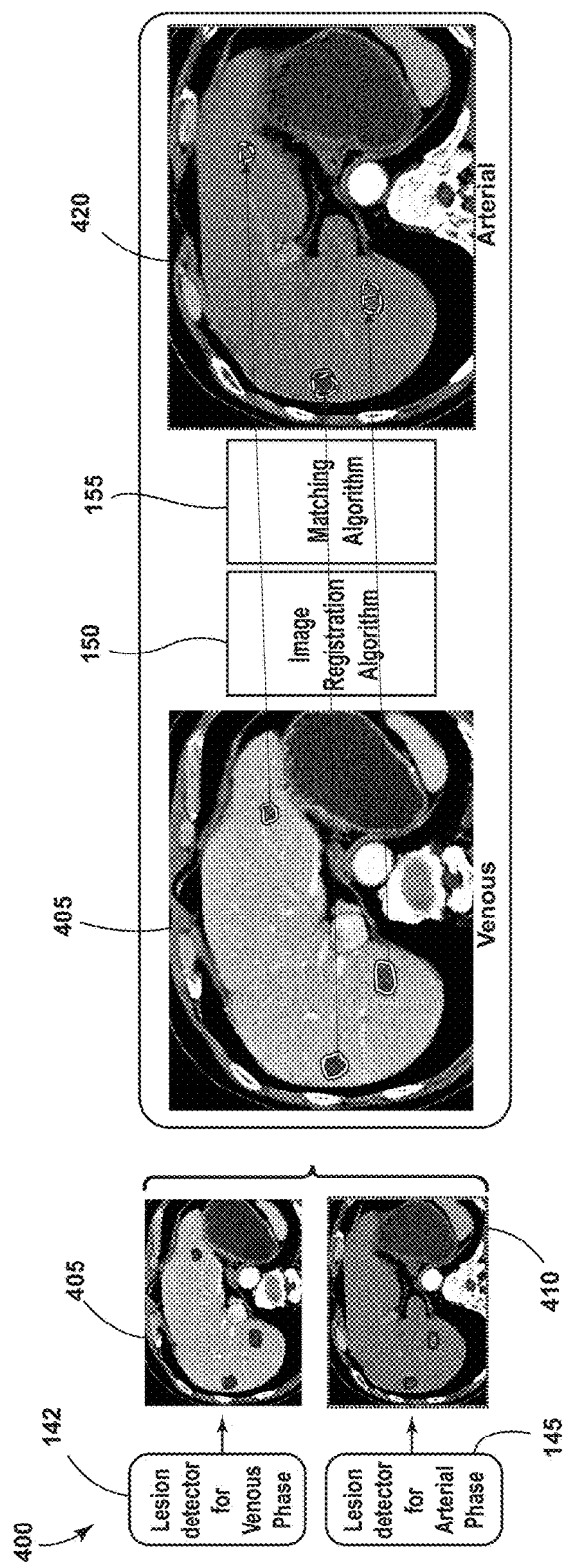
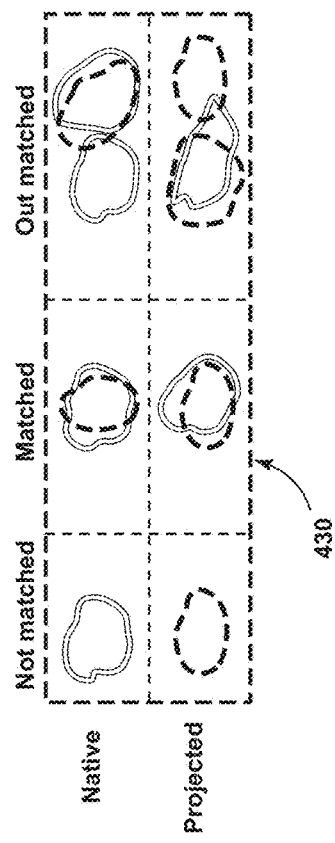
FIG. 4
FIG. 4A
FIG. 4B

METHODS AND SYSTEMS FOR DETECTING FOCAL LESIONS IN MULTI-PHASE OR MULTI-SEQUENCE MEDICAL IMAGING STUDIES

FIELD

Embodiments described herein relate to systems and methods for performing image analytics to define the presence and contour of lesions in multi-phase or multi-sequence medical images.

SUMMARY

Determining a presence and contour of lesions in multi-phase or multi-sequence imaging can be challenging. The main goal is to detect all lesions present in all phases (or sequences) while avoiding false positive detections. Optimizing a registration algorithm and a matching algorithm to map lesions across phases or sequences may improve the ability to detect and contour lesions in such studies. In a sample set of multi-phase liver studies with venous and arterial phases for focal liver lesion detection, 12% of lesions were only visible in the arterial phase (i.e., exhibited visible enhancement patterns). Accordingly, an approach to discover such lesions is important.

One embodiment provides a system for detecting lesions in multi-phase or multi-sequence medical imaging studies of medical images. The system includes at least one memory for storing medical images, and an electronic processor. The electronic processor is configured to: detect native candidate lesions for first phase computer tomography (CT) scans; detect candidate lesions for second phase CT scans; project the candidate lesions detected for the first phase CT scans and/or the second phase CT scans on a same domain; once the native candidate lesions and the candidate lesions are registered together, perform a matching algorithm for each of the native candidate lesions of the first phase CT scans with the registered candidate lesions from the second phase CT scans to determine presence and contours of valid lesions for the medical images, and to discard candidate lesions that are not acceptable; and provide or store the presence and the contours of the valid lesions.

Another embodiment provides a method for detecting lesions in multi-phase or multi-sequence medical imaging studies of medical images. The method includes: detecting native candidate lesions for first phase CT scans; detecting candidate lesions for second phase CT scans; projecting the candidate lesions detected for the first phase CT scans and/or the second phase CT scans on a same common domain; once the native candidate lesions and the candidate lesions are registered together, performing a matching algorithm with an electronic processor for each of the native candidate lesions of the first phase CT scans with the registered candidate lesions from the second phase CT scans to determine presence and contours of valid lesions for the medical images, and to discard candidate lesions that are not acceptable; and providing or storing the presence and the contours of the valid lesions.

A further embodiment provides a non-transitory computer medium including instructions that are executed as a set of instructions by an electronic processor performing a set of operations. The operations include: detecting native candidate lesions for first phase CT scans; detecting candidate lesions for second phase CT scans; projecting the candidate lesions detected for the first phase CT scans and/or the second phase CT scans on a same common domain; once the native candidate lesions and the candidate lesions are registered together, performing a matching algorithm for each of the native candidate lesions of the first phase CT scans with the registered candidate lesions from the second phase CT scans to determine presence and contours of valid lesions for the medical images, and to discard candidate lesions that are not acceptable; and providing or storing the presence and the contours of the valid lesions.

Other aspects of the invention will become apparent by consideration of the detailed description and accompanying drawings.

BRIEF DESCRIPTION OF THE DRAWINGS

FIG. 4 shows an operating example of analyzing CT scans for a liver lesion detection in multi-phase computed tomography.

FIG. 4A shows image registration of candidate lesions from a venous phase onto candidate lesions of an arterial phase CT scan.

FIG. 4B shows examples for native and projected candidate lesions that are not matched, matched, and out matched.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

A plurality of hardware and software-based devices, as well as a plurality of different structural components may be utilized to implement the invention. In addition, embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the invention may be implemented in software (e.g., stored on non-transitory computer-readable medium) executable by one or more processors. As such, it should be noted that a plurality of hardware and software-based devices, as well as a plurality of different structural components, may be utilized to implement the invention. For example, "mobile device," "computing device," and "server" as described in the specification may include one or more electronic processors, one or more memory modules including non-transitory computer-readable medium, one or more input/output interfaces, and various connections (e.g., a system bus) connecting the components.

Figure 1:
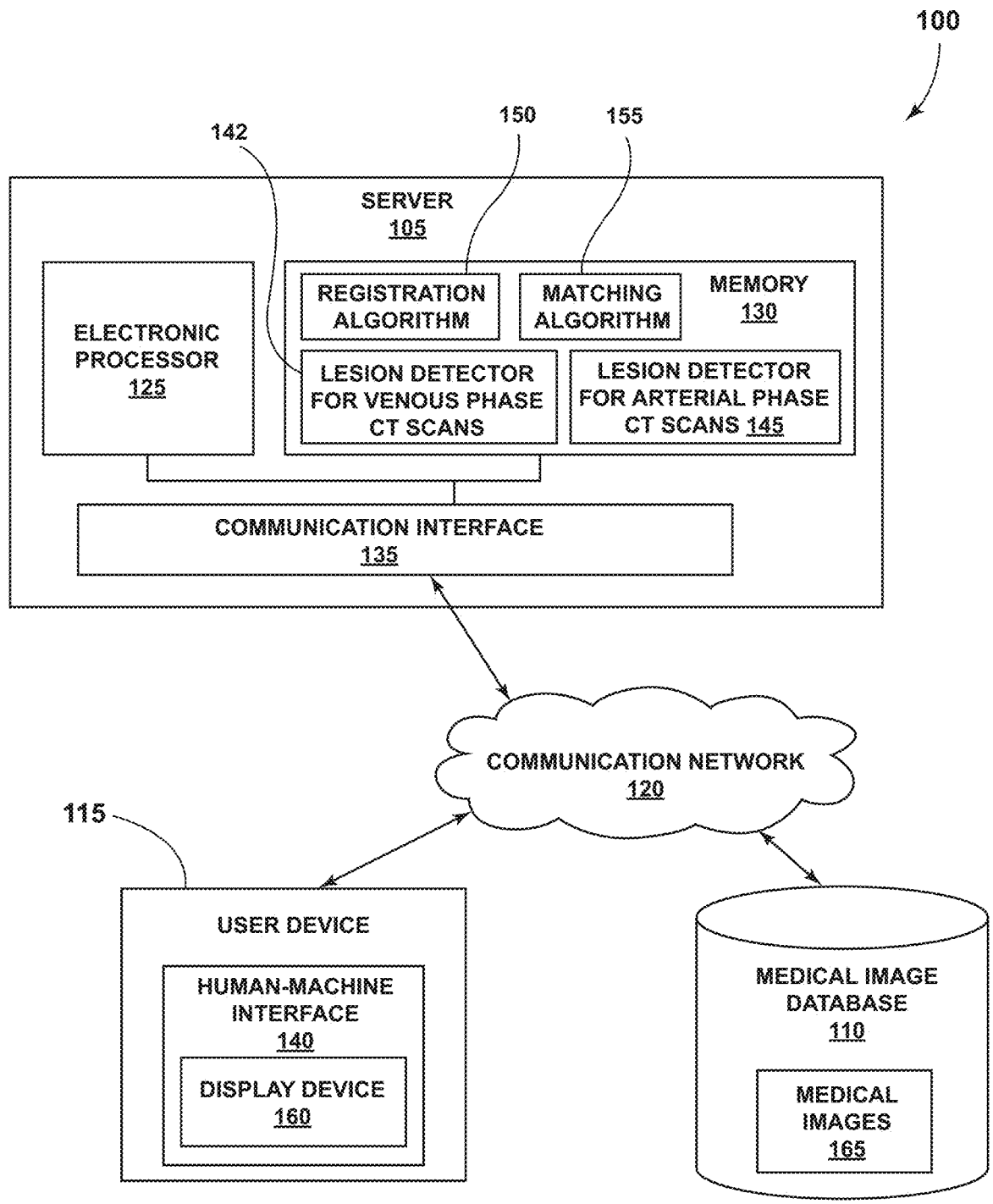
FIG. 1 illustrates a block diagram of a system for operating an artificial intelligence engine (AI) according to some embodiments for detecting and fusing focal lesions in multi-phase or multi-sequence medical imaging studies.

FIG. 1 illustrates a system 100 for an artificial intelligence (AI) engine according to some embodiments. The system 100 includes a server 105, a medical image database 110, and a user device 115. In some embodiments, the system 100 includes fewer, additional, or different components than illustrated in FIG. 1. For example, the system 100 may include multiple servers 105, medical image databases 110, user devices 115, or a combination thereof.

The server 105, the medical image database 110, and the user device 115 communicate over one or more wired or wireless communication networks 120. Portions of the communication network 120 may be implemented using a wide area network, such as the Internet, a local area network, such as a Bluetooth™ network or Wi-Fi, and combinations or derivatives thereof. Alternatively or in addition, in some embodiments, components of the system 100 communicate directly as compared to through the communication network 120. Also, in some embodiments, the components of the system 100 communicate through one or more intermediary devices not illustrated in FIG. 1.

The server 105 is a computing device, which may serve as a gateway for the medical image database 110. For example, in some embodiments, the server 105 may be a commercial picture archive and communication system (PACS) server. Alternatively, in some embodiments, the server 105 may be a server that communicates with a PACS server to access the medical image database 110.

As illustrated in FIG. 1, the server 105 includes an electronic processor 125, a memory 130, and a communication interface 135. The electronic processor 125, the memory 130, and the communication interface 135 communicate wirelessly, over one or more communication lines or buses, or a combination thereof. The server 105 may include additional components than those illustrated in FIG. 1 in various configurations. The server 105 may also perform additional functionality other than the functionality described herein. Also, the functionality described herein as being performed by the server 105 may be distributed among multiple devices, such as multiple servers included in a cloud service environment. In addition, in some embodiments, the user device 115 may be configured to perform all or a portion of the functionality described herein as being performed by the server 105.

The electronic processor 125 includes a microprocessor, an application-specific integrated circuit (ASIC), or another suitable electronic device for processing data. The memory 130 includes a non-transitory computer-readable medium, such as read-only memory (ROM), random access memory (RAM) (for example, dynamic RAM (DRAM), synchronous DRAM (SDRAM), and the like), electrically erasable programmable read-only memory (EEPROM), flash memory, a hard disk, a secure digital (SD) card, another suitable memory device, or a combination thereof. The electronic processor 125 is configured to access and execute a set of computer-readable instructions ("software") stored in the memory 130. The software may include firmware, one or more applications, program data, filters, rules, one or more program modules, and other executable instructions. For example, the software may include a set of instructions and associated data for performing a set of functions, including the methods described herein. The software may function as a neural network in some embodiments.

For example, as illustrated in FIG. 1, the memory 130 may store a candidate lesion detector for venous phase 142, a candidate lesion detector for arterial phase 145, a registration algorithm 150, and a matching algorithm 155 for matching the candidate lesions. It should be understood that in some embodiments, the algorithms 150, 155 may be located external to the server 105. In this embodiment, the server 105 may communicate with and access data from the algorithms 150, 155 directly or through one or more of the communication network(s) 120. Also, in some embodiments, the algorithms 150, 155 may be included in or part of the medical image database 110, the user device 115, or a combination thereof, which the server 105 may similarly access.

The communication interface 135 allows the server 105 to communicate with devices external to the server 105. For example, as illustrated in FIG. 1, the server 105 may communicate with the medical image database 110 through the communication interface 135. In particular, the communication interface 135 may include a port for receiving a wired connection to an external device (for example, a universal serial bus (USB) cable and the like), a transceiver for establishing a wireless connection to an external device (for example, over one or more communication networks 120, such as the Internet, local area network (LAN), a wide area network (WAN), and the like), or a combination thereof.

The server 105 may also communicate with user device 115 via the communication network 120. Broadly, a user, such as a clinician, uses user device 115 to interact with one or more of the candidate lesion detector for venous phase 142, the candidate lesion detector for arterial phase 145, the registration algorithm 150, the matching algorithm 155, and the medical image database 110. Although not illustrated, the user device 115 may include similar components as the server 105 (an electronic processor, a memory, and a communication interface). As noted above, in some embodiments, a memory of the user device 115 may store the registration algorithm 150, and/or the matching algorithm 155. Alternatively or in addition, the user device 115 may access the candidate lesion detector for venous phase 142, the candidate lesion detector for arterial phase 145, the registration algorithm 150, the matching algorithm 155 (or a portion thereof) stored in the memory 130 of the server 105 (or another device external to the user device 115) via the communication network 120.

The user device 115 may also include a human-machine interface 140. The human-machine interface 140 may include one or more input devices, one or more output devices, or a combination thereof. Accordingly, in some embodiments, the human-machine interface 140 allows a user to interact with (for example, provide input to and receive output from) the user device 115. For example, the human-machine interface 140 may include a keyboard, a cursor-control device (for example, a mouse), a touch screen, a scroll ball, a mechanical button, a display device (for example, a liquid crystal display (LCD)), a printer, a speaker, a microphone, or a combination thereof. As illustrated in FIG. 1, in some embodiments, the human-machine interface 140 includes a display device 160. The display device 160 may be included in the same housing as the user device 115 or may communicate with the user device 115 over one or more wired or wireless connections. For example, in some embodiments, the display device 160 is a touchscreen included in a laptop computer or a tablet computer. In other embodiments, the display device 160 is a monitor, a television, or a projector coupled to a terminal, desktop computer, or the like via one or more cables.

The medical image database 110 stores a plurality of medical images 165. As noted above, in some embodiments, the medical image database 110 is combined with the server 105. Alternatively or in addition, the medical images 165 may be stored within a plurality of databases, such as within a cloud service. Although not illustrated in FIG. 1, the medical image database 110 may include components similar to the server 105, such as an electronic processor, at least one memory, a communication interface, and the like. For example, the medical image database 110 may include a communication interface configured to communicate (for example, receive data and transmit data) over the communication network 120.

In some embodiments, the medical image database 110 stores additional data associated with the medical images 165, such as a classification associated with each of the medical images 165. In other embodiments, this information (along with the associated image data) may be stored separate from the medical image database 110. The medical image database 110 may also store acquired or captured medical images that are not part of a training dataset.

A learning engine applies machine learning (artificial intelligence) to mimic cognitive functions, including but not limited to learning and problem solving. Machine learning generally refers to the ability of a computer program to learn without being explicitly programmed. In some embodiments, a computer program (sometimes referred to as a learning engine) is configured to construct a model (for example, one or more algorithms) based on example inputs. Supervised learning involves presenting a computer program with example inputs and their desired (actual) outputs.

Machine learning may be performed using various types of methods and mechanisms. Example methods and mechanisms include decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using some or all of these approaches, a computer program may ingest, parse, and understand data and progressively refine models for data analytics, including image analytics. Once trained, the computer system may be referred to as an intelligent system, an artificial intelligence (AI) system, a cognitive system, or the like. Accordingly, in some embodiments, a learning engine includes Watson™ provided by IBM Corporation. A learning engine may be "trained" using various machine learning techniques. The learning engine may be utilized to determine the registration algorithm 150 and the matching algorithm 155. In one embodiment, the matching algorithm 155 is a Hungarian matching algorithm. The candidate lesion detectors 142, 145, the registration algorithm 150, and the matching algorithm 155 are operated to improve the discovery of valid lesions and the contours of valid lesions provided in images as follows.

Figure 2:
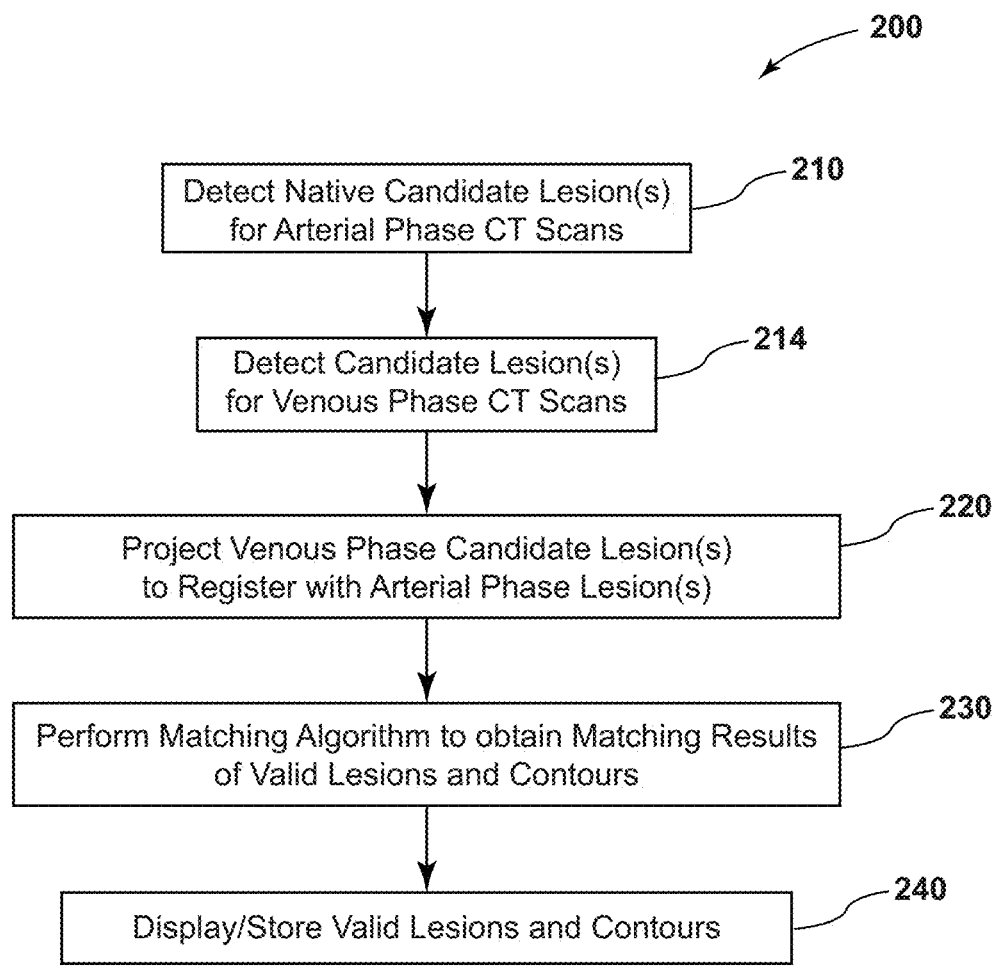
FIG. 2 shows a flowchart for determining valid lesions and contours from native candidate lesions for arterial computed tomography (CT) scans and registered candidate lesions from venous phase CT scans.

FIG. 2 shows a flowchart 200 for operation of the system 100 to detect focal lesions. The server 105 (i.e., the electronic processor 125) executes a set of instructions for determining the presence and contour of valid lesions as follows. The electronic processor 125 automatically selects, arranges, and processes medical images according to some embodiments. As noted above, in some embodiments, the user device 115 may be configured to execute one or more software applications to perform all or a portion of the functionality described herein as being performed via execution of the candidate lesion detectors 142, 145, the registration algorithm 150, and the matching algorithm 155.

In FIG. 2, the electronic processor 125 is configured to detect native candidate lesion(s) for an arterial phase of computer tomography (CT) scans of an image at step 210. The electronic processor 125 advances to step 214 and detects candidate lesion(s) for corresponding venous phase CT scans. The electronic processor 125 advances to step 220 to register the candidate lesion(s) of the venous phase of the CT scans with the native candidate lesion(s) of the arterial phase CT scans. Thus, the native candidate lesions and the candidate lesions of the venous phase are registered together.

Thereafter, the electronic processor 125 performs a matching algorithm at step 230 in FIG. 2 for each of the candidate lesions of the arterial phase CT scans with the registered candidate lesions from the venous phase CT scans to determine presence and contours of valid lesions for the CT scans of a medical image, and to discard candidate lesions that are not acceptable. The electronic processor 125 then displays and or stores the presence and contours of the valid lesions with the CT scans at step 240.

The arrangement shown in FIG. 2 is repeated for a plurality of CT scans of the medical images.

Figure 3:
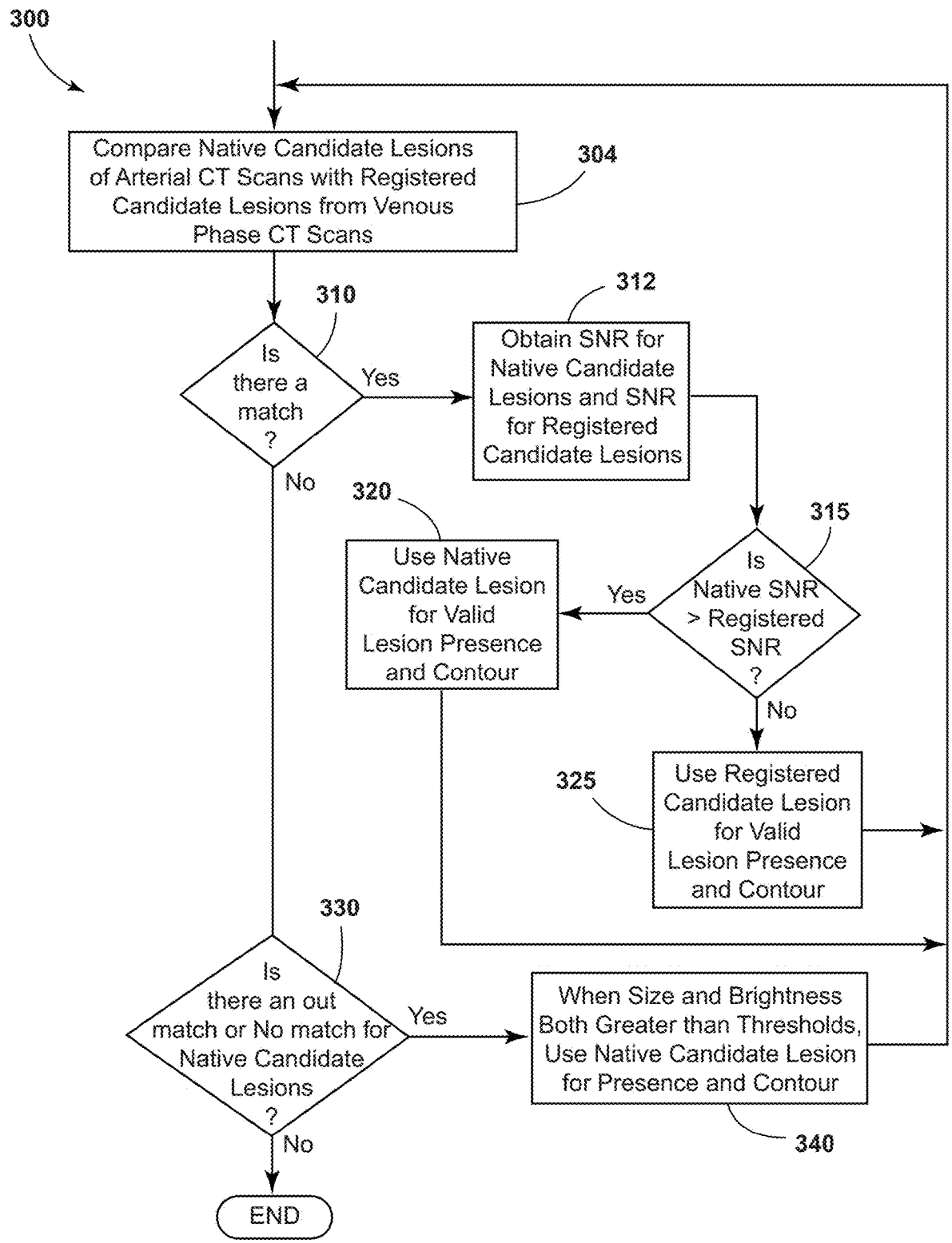
FIG. 3 illustrates a flowchart for one embodiment of a matching algorithm for matching the candidate lesions to determine valid lesions and contours in each phase or sequence.

The flowchart 300 of FIG. 3 provides a more detailed explanation for the electronic processor 125 executing the matching algorithm 155 as shown at step 230 in FIG. 2. At initial step 304, the electronic processor 125 is configured to compare native candidate lesions of the arterial phase CT scans with registered venous phase CT scans having candidate lesions to determine whether there is a candidate lesion from the registered venous phase CT scan disposed near the native candidate lesion from the arterial phase CT scan. The matching algorithm advances to decision step 310. At decision step 310, the electronic processor 125 determines whether there is a match between the native candidate lesion and the candidate lesion from the registered venous phase CT scans. If there is a match, the electronic processor 125 advances to step 312.

At step 312, the electronic processor 125 determines the enhancement/brightness (hereinafter "brightness") and the size of the native candidate lesions and the brightness and size of the corresponding registered candidate lesions from the venous phase scans. The electronic processor 125 determines a signal to noise ratio (SNR) for the matched candidates lesions as discussed in detail below. Thereafter, the electronic processor 125 advances to decision step 315.

At decision step 315, the SNR for the native candidate lesion is compared with the SNR for the corresponding matched registered candidate lesion. When the SNR of the native candidate lesion is greater than the SNR for the registered candidate lesion, decision step 315 advances to step 320. At step 320, the electronic processor 125 uses or selects the native candidate lesion to provide a presence and contour for the valid lesion. Thereafter, the matching algorithm 155 returns to beginning step 304.

At decision step 315, when the SNR for the native candidate lesion is not greater than the SNR for the matching registered candidate lesion, decision step 315 advances to step 325. At step 325, the electronic processor 125 is configured for using or selecting the registered candidate lesion to provide a presence and contour for the valid lesion. Thereafter, the matching algorithm 155 returns to beginning step 304.

Returning to decision step 310, in the instance there is not a match, the electronic processor 125 advances to decision step 330. At decision step 330, the electronic processor 125 determines whether there is an out match or no match for a native arterial candidate lesion. Specifically, the electronic processor 125 determines whether there is a native candidate lesion that is far from a registered candidate lesion in the corresponding venous phase CT scans. If so, the matching algorithm advances to step 340. At step 340, the electronic processor 125 determines whether the brightness and the size of the native candidate lesion is greater than a size threshold corresponding to a valid lesion and whether the brightness is greater than a brightness threshold corresponding to a valid lesion. If so, the native candidate lesion provides a presence and a contour for a valid lesion. If not, the electronic processor 125 is configured for discarding the candidate lesions that are not acceptable. Thus, the electronic processor 125 is configured to determine whether brightness of the native candidate lesion is greater than a brightness threshold and whether a size of the native candidate lesion is greater than a size threshold corresponding to a valid lesion even when there is no match. Thereafter, the electronic processor 125 returns to step 304 to analyze another native candidate lesion from the arterial phase CT scans.

In one embodiment, to provide a valid lesion result, the brightness must be greater than 5 Hounsfield unit (HU) and a diameter of the native candidate lesion must be greater than about 10 millimeters, so that the native candidate lesion is a valid lesion and the presence and contours of the native candidate lesion are stored. Other embodiments having different HU and different diameters are contemplated.

Returning to decision step 330, when the electronic processor 125 determines that no native candidate lesions remain for analysis, the matching algorithm 155 advances to step 350, wherein the matching algorithm analysis is completed.

Signal to Noise Ratio

Figure 3A:
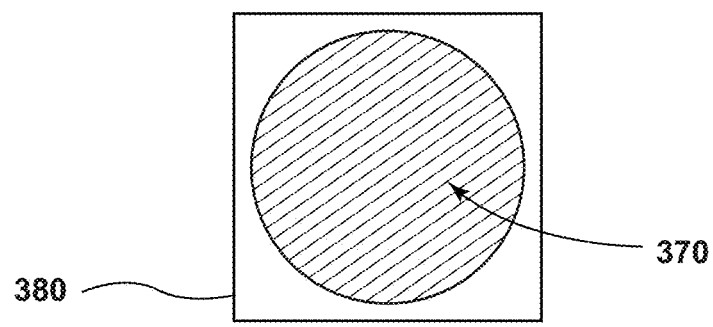
FIG. 3A illustrates a candidate lesion and a background box for calculating signal to noise ratio.

Return to step 312, the SNR is determined for the matching candidate lesions as shown in the two dimensional illustration of FIG. 3A. In one embodiment, a candidate lesion 370 is provided bounded in a background box 380. The area of the background box 380 is the bound area minus the area of the candidate lesion 370 illustrated in FIG. 3A. Thus, the candidate lesion 370 is represented by the shaded circle. The background box 380 is the rectangle without the lesion itself (the white area within the rectangle).

To determine SNR, first a contrast noise ratio (CNR) is determined or computed by the electronic processor 125 as follows. The following quantities are computed $\mu_B$ is average pixel intensity of the CT image area corresponding to the area of the background box 380 less the candidate lesion 370. $\mu_c$ is average pixel intensity of the CT image area corresponding to the area of the candidate lesion only. $\sigma_B$ is a standard deviation of the pixel intensity of the CT image area corresponding to the area of the background box 380 less the candidate lesion 370. The equation for CNR is as follows:

$$CNR=|\mu_c-\mu_B|/\sigma_B.$$

The signal to noise ratio (SNR) is based on the contrast noise ratio (CNR) times a variation of size of the candidate lesion. In one embodiment, the signal to noise equation is:

$SNR=CNR \times S^\alpha$ wherein S represents size and $\alpha$ represents alpha. In one embodiment, alpha is 0.5. In other embodiments, alpha is between 0 and 1.

Utilizing the above equations, separate values for the native candidate lesion and the matching registered candidate lesion from the venous phase are determined in step 312 shown in FIG. 3. A comparison as made at decision step 315 to select one of the candidate lesions.

Accordingly, the matching algorithm 155 matches each of the native candidate lesions of the arterial phase CT scans with the registered candidate lesions from the venous phase CT scans to select presence and contours of valid lesions for the medical images from the corresponding matched candidate lesions having a greater signal to noise ratio.

In other embodiments, performing the matching algorithm 155 for each of the native candidate lesions of the arterial phase CT scans with the registered candidate lesions from the venous phase CT scans to determine presence and contours of valid lesions for the medical images includes merging/fusing the native candidate lesions and the registered candidate lesions from the venous phase CT scans. The merging/fusing results in a valid lesion and determined contour. Thus, the merging of the native candidate lesions from the arterial phase CT scans and the registered candidate lesions from the venous phase CT scans results in a final single multi-phase lesion map.

The analysis of candidate lesions from CT scans is repeated for a plurality of CT scans corresponding to a volume. Thereafter, the electronic processor 125 is configured to sequentially determine and use or store the presence and contours of the valid lesions for a plurality of arterial phase CT scans and a plurality of registered venous phase CT scans to obtain a three-dimensional valid lesion contour.

Example

FIG. 4 shows an operating example 400 of analyzing CT scans for liver lesion detection in a multi-phase computed tomography. The candidate lesion detector for venous phase 142 detects a CT scan 405 showing three candidate lesions. The candidate lesion detector for arterial phase 145 detects a CT scan 410 showing two candidate lesions.

FIG. 4A shows the CT scan 405 of the venous phase projected by the registration algorithm 150 and the matching algorithm 155 onto the CT scan 410 in the arterial phase resulting in the image 420 showing the projection of the CT scan 405 in the venous phase having candidate lesions onto the CT scan with native candidate lesions in the arterial phase.

The resulting image 420 shows two of the candidate lesions in the venous phase projected onto and registered with two corresponding native candidate lesions in the venous phase. One projected candidate lesion from the venous phase is registered entirely away from the native candidate lesions shown in the resulting image 420.

FIG. 4B shows a table 430 with examples of not matched, matched, and out matched candidate lesions. The projected and registered candidate lesions in the venous phase are illustrated in broken line and the native candidate lesions from the arterial phase are shown in solid line.

Figure 5:
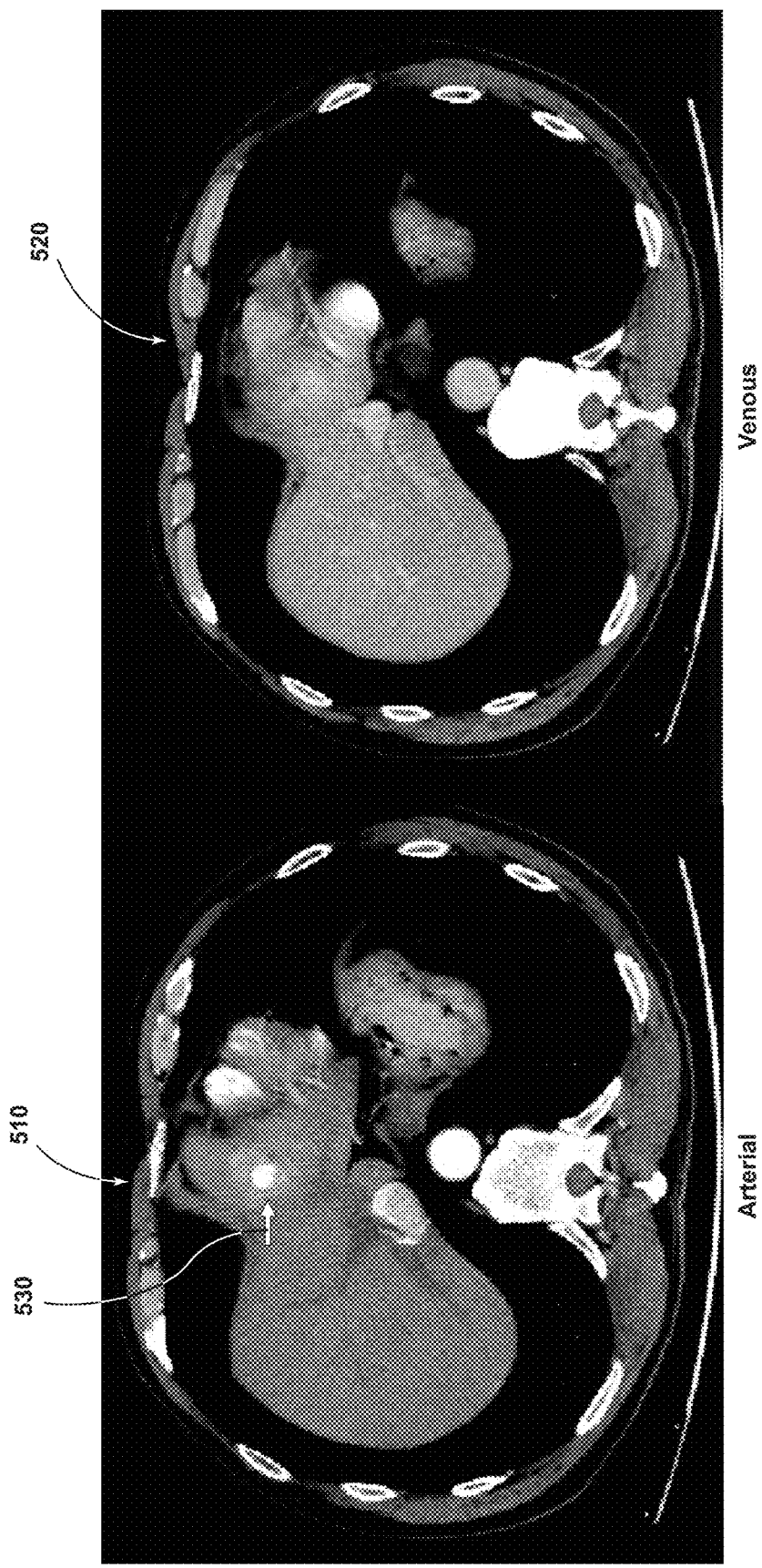
FIG. 5 shows a CT scan including a lesion that is difficult to detect as visibility is only provided in the arterial phase.

FIG. 5 shows a CT scan 510 in the arterial phase and a corresponding CT scan 520 in the venous phase. Arrow 530 in CT scan 510 points at a bright candidate lesion that is not really visible in the CT scan 520 in the venous phase. Thus, the disclosed arrangement set forth above operates so that a native candidate lesion in the arterial phase is a valid lesion having a contour in some instances. More specifically, in this example, the candidate lesion on the arterial scan would be accepted or validated as a valid lesion if its brightness and size meet the acceptance criteria (step 340 of FIG. 3).

In the above described embodiments, the arterial phase is a common domain that the venous phase is projected onto. Other arrangements are contemplated, wherein the common domain is the venous phase, a pre-contrast phase, or a delayed phase. In other embodiments, the arterial phase and/or the venous phase discussed above are replaced with any one from the group consisting of a pre-contrast phase, or a delayed phase. Thus, a first phase is defined as any one of an arterial phase, a venous phase, a pre-contrast phase, and a delayed phase. A second phase is defined as any one of an arterial phase, a venous phase, a pre-contrast phase, and a delayed phase that is different than the first phase.

In another embodiment, the common domain is an arbitrary common domain that has both the arterial phase and the venous phase set forth above, both projected thereon. In other embodiments, any two of the arterial phase, the venous phase, the pre-contrast phase, and the delayed phase are both projected onto the arbitrary common domain.

While an electronic processor 125 is mentioned above as executing the steps shown in FIG. 3, a neural network that is a set of mathematical operations can be performed partly or entirely on one or more servers 105 or other computing devices. In another embodiment, the neural network is provided on a single computing device. In another embodiment, the electronic processor 125 is a node implementing operation of the neural network.

Thus, embodiments described herein provide, among other things, methods and systems for providing projection of a registered candidate lesion from the venous phase onto a CT scan in the arterial phase. Machine learning techniques may be used to establish or modify a registration algorithm 150 for projecting the registered candidate lesions and a matching algorithm for comparing the registered candidate lesions and the native candidate lesions, which further improve the efficiency and effectiveness of the systems and methods. Various features and advantages of the invention are set forth in the following claims.

What is claimed is:

1. A system for detecting lesions in multi-phase or multi-sequence medical imaging studies of medical images, the system comprising:
   at least one memory for storing medical images; and
   an electronic processor configured to:
   detect native candidate lesions for first phase computer tomography (CT) scans;
   detect candidate lesions for second phase CT scans;
   project the candidate lesions detected for the first phase CT scans and/or the second phase CT scans on a same common domain;
   once the native candidate lesions and the candidate lesions are registered together, perform a matching algorithm for each of the native candidate lesions of the first phase CT scans with the registered candidate lesions from the second phase CT scans to determine presence and contours of valid lesions for the medical images, and to discard the candidate lesions that are not acceptable; and
   provide or store the presence and the contours of the valid lesions.

2. The system of claim 1, wherein the performing of the matching algorithm by the electronic processor includes
   determining whether there is a match between the native candidate lesions for the first phase CT scans and the corresponding registered candidate lesions from the second phase CT scans, wherein when there is a match, determining a signal to noise ratio (SNR) for the native candidate lesions and a SNR for the registered candidate lesions, and selecting the presence and the contours of the valid lesions from the corresponding matched candidate lesions having a greater signal to noise ratio;
   determining whether there is an out match of the native candidate lesions for the first phase CT scans; and
   when there is no match or out match, determining whether the brightness and the size of the native candidate lesion is greater than a size threshold corresponding to a valid lesion and whether the brightness is greater than a brightness threshold corresponding to a valid lesion.

3. The system of claim 2, wherein when there is no match or out match, and the brightness is not greater than the brightness threshold or the size of the native candidate lesion is not greater than the size threshold, the electronic processor is configured to discard the native candidate lesion, and wherein the first phase CT scans are arterial phase CT scans, the second phase CT scans are venous phase CT scans, and the common domain is the arterial phase.

4. The system of claim 1, wherein the electronic processor is configured to determine whether brightness of the native candidate lesion is greater than a brightness threshold and whether a size of the native candidate lesion is greater than a size threshold corresponding to a valid lesion even when there is no match.

5. The system of claim 1, wherein the electronic processor is configured to sequentially determine and store the presence and the contours of the valid lesions for a plurality of first phase CT scans and for a plurality of registered second phase CT scans to obtain a three dimensional valid lesion contour.

6. The system of claim 1, wherein performing the matching algorithm for each of the native candidate lesions of the first phase CT scans with the registered candidate lesions from the second phase CT scans to determine the presence and the contours of the valid lesions for the medical images includes merging/fusing the native candidate lesions and the registered candidate lesions from the second phase CT scans.

7. The system of claim 6, wherein the merging of the native candidate lesions from the first phase CT scans and the registered candidate lesions from the second phase CT scans results in a final single multi-phase lesion map, and wherein the first phase CT scans are arterial phase CT scans, the second phase CT scans are venous phase CT scans, and the common domain is the arterial phase.

8. A method for detecting lesions in multi-phase or multi-sequence medical imaging studies of medical images, the method comprising:
   detecting native candidate lesions for first phase CT scans;
   detecting candidate lesions for second phase CT scans;
   projecting the candidate lesions detected for the first phase CT scans and/or the second phase CT scans on a same common domain;
   once the native candidate lesions and the candidate lesions are registered together, performing a matching algorithm with an electronic processor for each of the native candidate lesions of the first phase CT scans with the registered candidate lesions from the second phase CT scans to determine presence and contours of valid lesions for the medical images, and to discard the candidate lesions that are not acceptable; and providing or storing the presence and the contours of the valid lesions.

9. The method of claim 8, wherein the performing of the matching algorithm by the electronic processor includes determining whether there is a match between the native candidate lesions for the first phase CT scans and the corresponding registered candidate lesions from the second phase CT scans, wherein when there is a match, determining a signal to noise ratio (SNR) for the native candidate lesions and a SNR for the corresponding registered candidate lesions, and selecting the presence and the contours of the valid lesions from the corresponding matched candidate lesions having a greater signal to noise ratio;

determining whether there is an out match of the native candidate lesions for the first phase CT scans; and when there is no match or out match, determining whether the brightness and the size of the native candidate lesion is greater than a size threshold corresponding to a valid lesion and whether the brightness is greater than a brightness threshold corresponding to a valid lesion.

10. The method of claim 9, wherein when there is no match or out match, and the brightness is not greater than the brightness threshold or the size of the native candidate lesion is not greater than the size threshold, the electronic processor is configured to discard the native candidate lesion, and wherein the first phase CT scans are arterial phase CT scans, the second phase CT scans are venous phase CT scans, and the common domain is the arterial phase.

11. The method of claim 8, wherein the electronic processor is configured to determine whether brightness of the native candidate lesion is greater than a brightness threshold and whether a size of the native candidate lesion is greater than a size threshold corresponding to a valid lesion even when there is no match.

12. The method according to claim 8, wherein the electronic processor is configured to sequentially determine and store the presence and contours of the valid lesions for a plurality of first phase CT scans and a plurality of registered second phase CT scans to obtain a three dimensional valid lesion contour.

13. The method according to claim 8, wherein performing the matching algorithm for each of the native candidate lesions of the first phase CT scans with the registered candidate lesions from the second phase CT scans to determine the presence and the contours of the valid lesions for the medical images includes merging/fusing the native candidate lesions and the registered candidate lesions from the second phase CT scans.

14. The method according to claim 13, wherein the merging of the native candidate lesions from the first phase CT scans and the registered candidate lesions from the second phase CT scans results in a final single multi-phase lesion map, and wherein the first phase CT scans are arterial phase CT scans, the second phase CT scans are venous phase CT scans, and the common domain is the arterial phase.

15. A non-transitory computer medium including instructions that, when executed as a set of instructions by an electronic processor perform a set of operations comprising:

detecting native candidate lesions for first phase CT scans;

detecting candidate lesions for second phase CT scans;

projecting the candidate lesions detected for the second phase CT scans to register with the first phase CT scans;

once the native candidate lesions and the candidate lesions are registered together, performing a matching algorithm for each of the native candidate lesions of the first phase CT scans with the registered candidate lesions from the second phase CT scans to determine presence and contours of valid lesions for the medical images, and to discard candidate lesions that are not acceptable; and providing or storing the presence and the contours of the valid lesions.

16. The non-transitory computer medium of claim 15, wherein the instructions executed by the electronic processor to perform the matching algorithm include determining whether there is a match between the native candidate lesions for the first phase CT scans and the corresponding registered candidate lesions from the second phase CT scans, wherein when there is a match, determining a signal to noise ratio (SNR) for the native candidate lesions and a SNR for the registered candidate lesions, and selecting the contours of the valid lesions from the corresponding matched candidate lesions having a greater signal to noise ratio;

determining whether there is an out match of the native candidate lesions for the first phase CT scans; and when there is no match or out match, determining whether the brightness and the size of the native candidate lesion is greater than a size threshold corresponding to a valid lesion and whether the brightness is greater than a brightness threshold corresponding to a valid lesion.

17. The non-transitory computer medium of claim 16, wherein the instructions executed by the electronic processor to perform the matching algorithm include when there is no match or out match, and the brightness is not greater than the brightness threshold or the size of the native candidate lesion is not greater than the size threshold, discarding the native candidate lesion, and wherein the first phase CT scans are arterial phase CT scans, the second phase CT scans are venous phase CT scans, and the common domain is the arterial phase.

18. The non-transitory computer medium of claim 15, wherein the instructions executed by the electronic processor to perform the matching algorithm include determining whether brightness of the native candidate lesion is greater than a brightness threshold and whether a size of the native candidate lesion is greater than a size threshold corresponding to a valid lesion even when there is no match.

19. The non-transitory computer medium of claim 15, wherein the instructions executed by the electronic processor sequentially determine and store the presence and the contours of the valid lesions for a plurality of first phase CT scans and a plurality of registered second phase CT scans to obtain a three dimensional valid lesion contour.

20. The non-transitory computer medium of claim 19, wherein the instructions executed by the electronic processor for performing the matching algorithm for each of the native candidate lesions of the first phase CT scans with the registered candidate lesions from the second phase CT scans to determine the presence and the contours of the valid lesions for the medical images includes merging/fusing the native candidate lesions and the registered candidate lesions from the second phase CT scans, and wherein the first phase CT scans are arterial phase CT scans, the second phase CT scans are venous phase CT scans, and the common domain is the arterial phase.

* * * * *